(12) United States Patent
Zhu (10) Patent No.: US 11,020,041 B2
(45) Date of Patent: Jun. 1, 2021

(54) INDIVIDUAL-CHARACTERISTIC-BASED TRANSCRANIAL BRAIN ATLAS GENERATION METHOD, NAVIGATION METHOD, AND NAVIGATION SYSTEM

(71) Applicant: BEIJING NORMAL UNIVERSITY, Beijing (CN)

(72) Inventor: Chaozhe Zhu, Beijing (CN)

(73) Assignee: BEIJING NORMAL UNIVERSITY, Beijing (CN)

( * ) Notice: Subject to any disclaimer, the term of this patent is extended or adjusted under 35 U.S.C. 154(b) by 241 days.

(21) Appl. No.: 16/314,644

(22) PCT Filed: Apr. 22, 2018

(86) PCT No.: PCT/CN2018/084000
§ 371 (c)(1),
(2) Date: Dec. 31, 2018

(87) PCT Pub. No.: WO2019/109575
PCT Pub. Date: Jun. 13, 2019

(65) Prior Publication Data
US 2019/0320966 A1    Oct. 24, 2019

(30) Foreign Application Priority Data

Dec. 5, 2017   (CN) .......................... 201711268640.0
Dec. 12, 2017  (CN) .......................... 201711322471.4

(51) Int. Cl.
*A61B 5/05*    (2021.01)
*A61B 5/00*    (2006.01)
(Continued)

(52) U.S. Cl.
CPC .............. *A61B 5/4064* (2013.01); *A61B 5/05* (2013.01); *G06F 3/03545* (2013.01);
(Continued)

(58) Field of Classification Search
CPC . A61B 5/4064; A61B 5/05; A61B 2560/0223; G06T 17/20; G06T 2210/41; G06T 2210/56
See application file for complete search history.

(56) References Cited

FOREIGN PATENT DOCUMENTS

| CN | 103932796 A | 7/2014 |
|---|---|---|
| CN | 104436443 A | 3/2015 |

(Continued)

OTHER PUBLICATIONS

International Search Report from PCT/CN2018/084000, dated Aug. 31, 2018, with English translation from WIPO.
(Continued)

*Primary Examiner* — Joel F Brutus
(74) *Attorney, Agent, or Firm* — Ladas & Parry, LLP (57) ABSTRACT

The present invention discloses an individual-level transcranial brain atlas generation method, where invisible intracerebral atlas information may be projected onto a visible scalp surface, so that an operational space and an effective space that are originally separated are fused together. For the problem of applying a transcranial brain atlas to guidance of individual placement of a transcranial device, the present invention further provides an individual-characteristic-based transcranial brain atlas generation method and navigation system. An experimental result indicates that, the present invention can be used to effectively improve coverage accuracy of a near-infrared measurement optrode in a brain region of interest, and consistency between measurement locations on upper cortexes of different persons, thereby improving sensibility of detecting a task-induced brain activity by using a near-infrared technology.

9 Claims, 6 Drawing Sheets
(5 of 6 Drawing Sheet(s) Filed in Color)

(51) Int. Cl.
*G06F 3/0354* (2013.01)
*G06T 17/20* (2006.01)

(52) U.S. Cl.
CPC ...... *G06T 17/20* (2013.01); *A61B 2560/0223* (2013.01); *G06T 2210/41* (2013.01); *G06T 2210/56* (2013.01)

(56) References Cited

FOREIGN PATENT DOCUMENTS

| | | |
|---|---|---|
| CN | 104474636 A | 4/2015 |
| EP | 2509013 A1 | 10/2012 |

OTHER PUBLICATIONS

Written Opinion of the International Searching Authority from PCT/CN2018/084000, dated Aug. 31, 2018, with machine English translation from Google Translate.

INDIVIDUAL-CHARACTERISTIC-BASED TRANSCRANIAL BRAIN ATLAS GENERATION METHOD, NAVIGATION METHOD, AND NAVIGATION SYSTEM

CROSS-REFERENCE TO RELATED APPLICATIONS

The present application is the U.S. national phase of PCT Application PCT/CN2018/084000 filed on Apr. 22, 2018, which claims priority to the Chinese patent application No. 201711268640.0 filed on Dec. 5, 2017, and Chinese patent application No. 201711322471.4 filed on Dec. 12, 2017, the entire disclosures of which are hereby incorporated by reference in their entireties.

BACKGROUND

Technical Field

The present invention relates to an individual-level transcranial brain atlas generation method, relates to an individual-characteristic-based transcranial brain atlas navigation method, and further relates to a corresponding individual-level transcranial brain atlas navigation system.

Related Art

Currently, an important task with which the cognitive neuroscience is confronted is to establish a correspondence between a brain function and a brain structure. Functional brain imaging technologies represented by the functional magnetic resonance imaging (MARI) and the functional near-infrared spectroscopy (fNIRS) enable researchers of the neuroscience to observe a function of a living human brain in a non-invasive manner.

Transcranial brain mapping technologies including transcranial brain treatment and transcranial brain imaging are always being rapidly developed, and present a huge potential in aspects of brain mechanism evaluation and brain damage treatment. For example, transcranial magnetic stimulation (TMS for short) suppresses or stimulates a local activity of a human brain at a high temporal-spatial resolution by using an externally applied magnetic field, A non-invasive characteristic of the transcranial magnetic stimulation makes the transcranial magnetic stimulation conductive to evaluation of a causal relationship between a particular brain region/brain circuit and a behavior. The transcranial magnetic stimulation is also widely used to treat various neuropsychiatric disorders such as the Parkinson's disease, aches, and habituation. It should be noted that, the transcranial magnetic stimulation as a clinic intervention means of treating the drug-resistant depression disorder is authenticated by the Food and Drug Administration (FDA).

A transcranial brain mapping technology is usually operated on a visible scalp surface (referred to as an operational space). However, target regions of transcranial brain treatment and transcranial brain imaging are located inside the brain (referred to as an effective space), which are invisible from the outside from the standpoint of an operator. Therefore, given a target location or a labeled brain region in the effective space, it is quite difficult to position an optimal imaging or stimulation site on an individual scalp surface. This may result in sub-optimized and inconsistent experimental results, and even conflicting conclusions. For example, the inconsistency in the placement of the coil for implementing the transcranial magnetic stimulation over the target region for treating depression (for example, the dorsolateral prefrontal cortex) may result in different treatment outcomes. Similarly, placement of an fNIRS optrode is also essential and critical. Improper placement may result in deviation of recording of a cortical location and even may cover an erroneous cortical region. Moreover, in group analysis in neural image research, imaging cortical locations from different individuals need to correspond to each other to compare results between the different individuals. Currently, it is still challenging to correctly place the fNIRS optrode on the scalp to cover a cortical region of interest and keep the correspondence between the imaging cortical locations from the different subject individuals, Separation between a visible operational space (scalp surface) and an invisible effective space (inside the brain) is still one of biggest challenges in effectively and accurately applying these transcranial brain mapping technologies.

SUMMARY

A primary technical problem to be resolved by the present invention is to provide an individual-level transcranial brain atlas generation method.

Another technical problem to be resolved by the present invention is to provide an individual-characteristic-based transcranial brain atlas navigation method.

Still another technical problem to be resolved by the present invention is to provide an individual-level transcranial brain atlas navigation system.

To achieve the foregoing objectives, the present invention uses the following technical solutions:

According to a first aspect of embodiments of the present invention, an individual-characteristic-based cranial surface coordinate system generation method is provided, including the following steps:

(11) identifying five cranial landmarks Nz, Iz, AL, AR, and Cz on an individual scalp surface;

(12) defining an intersection curve between the scalp surface and a plane passing through Nz, Cz, and Iz as a cranial equator;

(13) giving a point p on the scalp surface, where a longitude curve can be uniquely determined as an intersection curve between the scalp surface and a plane passing through AL, AR, and p, and p' is an intersection point between the cranial equator and the longitude curve; and (14) uniquely determining any point p on an upper scalp by using a pair of non-negative real numbers ($p_e$, $p_l$):

$$p_e = L_{NZ\text{-}p'} / L_c, p_e \in [0 1]$$

$$p_e = L_{AL\text{-}p} / L_{AL\text{-}p\text{-}AR}, p_l \in [0 1]$$

where $L_{NZ\text{-}p'}$ is a curve length from Nz to p' along the cranial equator, and $L_c$ is a full length of the cranial equator; and $L_{AL\text{-}p}$ is a curve length from AL to p along the longitude curve whose full length is $L_{AL\text{-}p\text{-}AR}$.

Preferably, the foregoing cranial surface coordinate system generation method further includes step (15): establishing a CPC space on a standard hemisphere; and planarizing a hemisphere having CPC coordinates by using a Hammer-Aitoff projection, to generate a map having a CPC coordinate system presented on a flat ellipse.

According to a second aspect of the embodiments of the present invention, an individual-characteristic-based transcranial brain atlas generation method is provided, including the following steps:

(1) creating a cranial surface coordinate system at an individual level according to the foregoing steps;

(2) establishing a transcranial mapping system used to connect a cranial location and a brain location; and (3) constructing a transcranial brain atlas by using a two-step stochastic process in a Markov chain.

Preferably, the step (2) includes the following substeps:

determining an underlying cortical location c corresponding to the given any point p on the scalp surface in an individual space by using a balloon inflation model; and after all cortical locations are spatially normalized into an MNI space, aggregating all (p, c) pairs, to generate a deterministic individual transcranial brain mapping model.

According to a third aspect of the embodiments of the present invention, an individual-characteristic-based transcranial brain atlas navigation method is provided, including the following steps:

(1) performing sparse uniform sampling of a plurality of points on a scalp surface of a subject, to reconstruct an approximate curved surface of the scalp surface of the subject;

(2) establishing a CPC coordinate system on the approximate curved surface; and (3) converting, in real time, a location of a stylus moving on the scalp surface of the subject into the CPC coordinate system in which the foregoing transcranial brain atlas is located, and guiding placement of a transcranial device on the scalp surface by using information about the transcranial brain atlas.

Preferably, in the step (1), the sampling points include two parts, a first part is 4 cranial landmarks Nz, Iz, AL, and AR, and a second part is collected by an operator manually on the scalp surface of the subject.

Preferably, discretized point clouds generated based on the sampling points are indicated in a nasal-fossa-preauricular coordinate system, where an origin O of the nasal-fossa-preauricular coordinate system is defined as a midpoint of an AL-AR connection line, and a direction from the point O to Nz is a positive direction of an axis X, a direction from the point O to AL is a positive direction of an axis Y, and a positive direction of an axis Z is defined as a direction of a cross product of the axis X and the axis Y.

Preferably, a topological connection between the discretized point clouds is reconstructed by using a CRUST algorithm, to obtain a triangle patch set $TP\{(i,j,k)|i,j,k=1, 2, \ldots M\}$, where i, j, and k are sequence numbers of the midpoint P respectively, and each triplet (i, j, k) indicates three points topologically neighboring.

Preferably, nonlinear interpolation is performed on all triangle patches in the triangle patch set $TP\{(i,j,k)|i,j,k=1, 2, \ldots M\}$, to obtain a subdivided triangle mesh; and vertexes on the triangle mesh are reserved and recorded as a dense point cloud $DP=\{x_i,y_i,z_i|i=1, 2, 3, \ldots, N_{DP}\}$, to serve as the approximate curved surface.

According to a fourth aspect of the embodiments of the present invention, an individual-level transcranial brain atlas navigation system is provided, including a processing component, a display component, a memory, a three-dimensional positioning component, and an input/output interface, where the processing component is connected to the three-dimensional positioning component, the display component, the memory, and the input/output interface, and is configured to perform all or some steps in the foregoing transcranial brain atlas navigation method;

the display component is connected to the three-dimensional positioning component, and is configured to display a current status of the three-dimensional positioning component on a scalp surface of a subject and a status of the three-dimensional positioning component in a transcranial brain atlas in real time;

the memory is configured to store various types of data;

the three-dimensional positioning component is configured to reconstruct an approximate curved surface of the scalp surface of the subject by using a plurality of points collected from the scalp surface of the subject; and the input/output interface is configured to connect the individual-level transcranial brain atlas navigation system to an external transcranial device.

Preferably, the three-dimensional positioning component is a three-dimensional magnetic-field locator, and includes a magnetic-field transmitter and two magnetic-field sensors, where one magnetic-field sensor is of a stylus shape, and the other magnetic-field sensor is of a cube shape.

Preferably, when the three-dimensional magnetic-field locator is used, the magnetic-field transmitter is fixed on a bracket behind the subject, the magnetic-field sensor of the cube shape is fixed at a zygomatic location of the subject, and the magnetic-field sensor of the stylus shape is held by an experimenter to calibrate a location on the scalp surface of the subject.

Compared with the prior art, the present invention first provides an individual-level transcranial brain atlas generation method, where invisible intracerebral atlas information may be projected onto a visible scalp surface, so that an operational space and an effective space that are originally separated are fused together. For the problem of applying a transcranial brain atlas to guidance of individual placement of a transcranial device, the present invention further provides an individual-level transcranial brain atlas navigation system. An experimental result indicates that, the present invention can be used to effectively improve coverage accuracy of a near-infrared measurement optrode in a brain region of interest, and consistency between measurement locations on upper cortexes of different persons, thereby improving sensibility of detecting a task-induced brain activity by using a near-infrared technology.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Technical content of the present invention is further described in detail below with reference to the accompanying drawings and specific embodiments.

As described above, separation between a cranial surface space visible to a transcranial imaging apparatus and an intracranial brain space invisible to the transcranial imaging apparatus is one of biggest challenges in effectively applying a transcranial brain mapping technology. To resolve a corresponding problem of the two spaces, the present invention first proposes a concept of a transcranial brain atlas (TBA for short). The transcranial brain atlas is a brain atlas established on a scalp surface. According to the transcranial brain atlas, invisible intracerebral atlas information is projected onto a visible scalp surface (particularly, upper scalp surface), so that a researcher or a doctor may directly use these pieces of atlas information related to the brain structure and the brain function.

Specifically, in the present invention, a standard cranial coordinate system is explicitly constructed first, and used to quantitatively describe cranial surface spaces for different individuals. Then, according to an assumption of consistency of a cranio cerebral correspondence at a population level, a correspondence between a standard cranial surface space and a standard brain space in which a brain atlas is located is established. Finally, according to the present invention, from two correspondences between the cranial surface space and the standard brain space, and between the standard brain space provided in the brain atlas and a brain region label space, a correspondence between the cranial surface space and the brain region label space is solved. As a result, in the present invention, information in the standard brain space and the brain atlas that are corresponding to each other is reversely presented to the cranial coordinate system, thereby forming a novel "transcranial brain atlas". The transcranial brain atlas has an important property of being capable of directly deducing information about a corresponding brain region label by using only information about a cranial location, and therefore may be roughly understood as a brain atlas established on a scalp surface. The transcranial brain atlas is substantially a brain function map established on a coordinate-based scalp surface. That is, in a coordinate-based brain space, a conventional brain atlas corresponds to each cerebral location and a functional or anatomical label thereof, thereby drawing cortical locations accessible to a transcranial brain mapping technology and atlas labels corresponding to the cortical locations, and clearly and definitely presenting them on the scalp surface as a visible operational space.

In the transcranial brain atlas, priori brain region information in the conventional brain atlas may be mapped to a cranial space used to place a transcranial brain imaging apparatus in the sense of a population-level craniocerebral correspondence. Therefore, the transcranial brain atlas may be considered as an extension of the conventional brain atlas in the field of transcranial brain imaging technologies. Under the framework of the transcranial brain atlas, positioning for transcranial data in the brain space may be converted into positioning for the transcranial imaging apparatus in the cranial space, so that real-time positioning of the transcranial brain mapping technology becomes possible. Moreover, label information of the transcranial brain atlas is displayed in the cranial space, and this characteristic greatly helps the transcranial brain atlas be superposed onto a scalp surface of an individual to perform display, thereby guiding placement of the transcranial imaging apparatus on a cranial surface of a subject in a visual manner. Therefore, establishment of the transcranial brain atlas resolves a contradiction of separation between the operational space and the effective space in the transcranial brain mapping technology.

Figure 1:
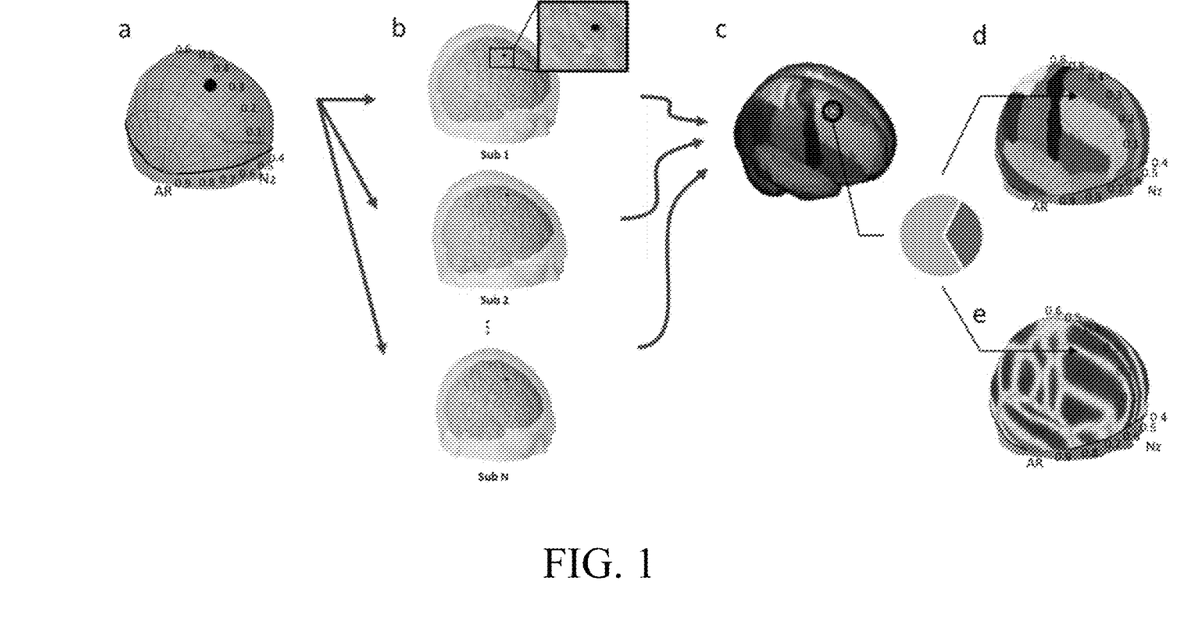
FIG. 1(a) to FIG. 1(e) are schematic diagrams of a series of embodiments of a transcranial brain atlas.

FIG. 1(a) to FIG. 1(e) are schematic diagrams of a series of embodiments of a transcranial brain atlas. As shown in FIG. 1(a), it is assumed that a unified cranial surface coordinate system is defined on a scalp surface. The cranial surface coordinate system describes all possible locations at which a probe for a transcranial brain mapping technology may be disposed, and the probe is disposed at a given cranial location (a location of a black point in the figure). For a particular individual (for example, a subject sub 1 in FIG. 1(b)), a probe disposed on a scalp surface of the subject can probe a particular cortical location/brain region (a location of a yellow point in the figure). However, at a group level, in consideration of a difference between anatomical structures across individuals, such a cranio-cerebral correspondence may not be deterministic. As shown in FIG. 1(c), after normalized into the standard brain space, the space distribution (that is, colored region within a black circle) of such a probabilistic correspondence is captured. By giving anatomical information obtained from the brain atlas, such a probabilistic correspondence can provide a group-level probability of how to access each brain region from a cranial location, and the group-level probability is used as priori knowledge. The transcranial brain atlas is substantially used for mapping the priori knowledge to the entire brain space defined by the cranial surface coordinate system, Specifically, in the series of embodiments shown in FIG. 1, if only a most possibly probed brain region label and a probability associated with the brain region label are considered for each cranial location, the maximum likelihood labeling map (MLM) shown in FIG. 1(d) and the maximum probability map (MPM) shown in FIG. 1(e) may be used as useful guidance for probe arrangement in the transcranial brain mapping technology.

In this embodiment of the present invention, a process of generating a transcranial brain atlas mainly includes three steps: (1) creating a cranial surface coordinate system at an individual level; (2) establishing a transcranial mapping system used to connect a cranial location and a brain location; and (3) constructing a transcranial brain atlas by using a two-step stochastic process in a Markov chain.

A detailed process for generating the transcranial brain atlas is described below.

(1) Create a cranial surface coordinate system at an individual level

The cranial surface coordinate system needs to satisfy two basic requirements: first, it should provide a one-to-one mapping for the individual scalp surface; and second, for the convenience of group-level studies, it should make, for each location in the cranial surface coordinate system, the underlying cortical locations from, different individuals basically consistent with each other neural-anatomically.

Figure 2:
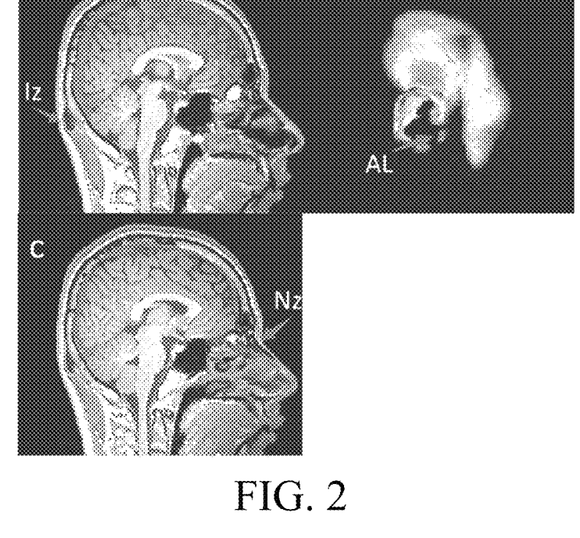
FIG. 2 is a schematic diagram of identifying a cranial landmark from a magnetic resonance image.
Figure 3:
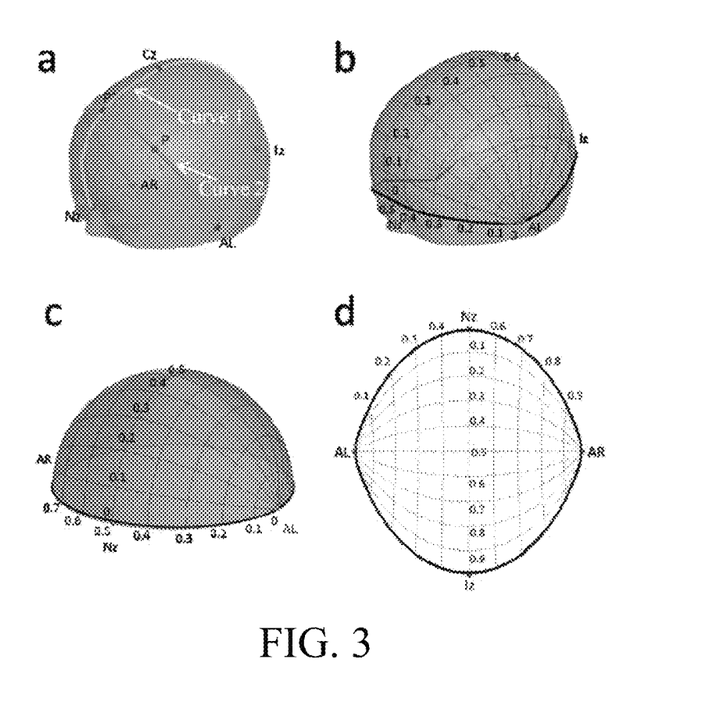
FIG. 3 is a schematic diagram of a CPC coordinate system.

The basic idea of the CPC coordinate system is to construct a coordinate system similar to longitude and latitude lines on a scalp surface. Different from a geographic longitude and latitude line system, the CPC coordinate system determines "longitude and latitude" in a manner of performing, surface proportion measurement twice. In this embodiment of the present invention, by using the following three steps, a two-dimensional proportional coordinate system referred to as a continuous proportional coordinate space (CPC space for short) is established on a scalp surface of an individual:

(11) At least five cranial landmarks Nz, Iz, AL, AR, and Cz derived from a 10-20 system are identified on a scalp surface of an individual space (referring to FIG. 3(a)). For an example of identifying a cranial landmark in a magnetic resonance image, refer to FIG. 2, where Iz is an external occipital protuberance of a human cranial bone onto which a trapezius is attached; AL and AR are left and right preauricular points that are identified as peak regions of tragi; Nz is identified as a dent location on a superior root of a nose bridge; and Cz is determined as an intersection point of cranial surface geodesics AL-Cz-AR and Nz-Cz-Iz, and equally divides the two cranial surface geodesics.

(12) A cranial equator is defined as an intersection curve (that is, a curve 1 in FIG. 3(a)) between the scalp surface and a plane passing through Nz, Cz, and Iz.

(13) A point p is given on the scalp surface, where a longitude curve (that is, a curve 2 in FIG. 3(a)) can be uniquely determined as an intersection curve between the scalp surface and a plane passing through AL, AR, and p, and p' is an intersection point between the cranial equator and the longitude curve.

On the basis of the three-step definition, any point p on an upper scalp (above the curve specified by the Nz, Iz, AL, and AR points) can be uniquely determined by using a pair of non-negative real numbers $(p_e, p_l)$:

$$p_e = L_{NZ-p'}/L_e, p_e \in [01] \quad (1)$$

$$p_l = L_{AL-p}/L_{AL-p-AR}, p_l \in [01] \quad (2)$$

where $L_{NZ-p'}$ is a curve length from Nz to p' along the cranial equator, and $L_e$ is a full length (from Nz to Iz) of the cranial equator; and $L_{AL-p}$ is a curve length from AL to p along the longitude curve whose full length is $L_{AL-p-AR}$. As shown in FIG. 3(b), a surface location of the p point as any point is uniquely indicated by proportions of p' and p respectively relative to the two curves. For calculation formulas, refer to the formula (1) and the formula (2).

FIG. 3(b) is a schematic diagram of a two-dimensional proportional coordinate system (CPC coordinate system for short) established on a scalp surface. The two-dimensional proportional coordinate system provides one-to-one mapping for any point p on the scalp surface to the CPC space. It may be learned from the foregoing description that, the CPC coordinate system is substantially to construct a coordinate system similar to longitude and latitude lines on a scalp surface. However, different from geographic longitude and latitude lines, the CPC coordinate system determines "longitude and latitude" in a manner of performing surface proportion measurement twice.

Based on an inter-subject correspondence established according to a proportional relationship defined between the cranial landmarks (Nz, Iz, AL, AR, and Cz) and the CPC coordinate system (proportional to the scale and the shape), a proper anatomical correspondence may be established on an individual-level scalp surface. To visualize the entire scalp surface from a single viewing angle, as shown in FIG. 3(c), a special CPC space is established on a standard hemisphere. Then, a hemisphere having a CPC coordinate system is planarized by using an existing Hammer-Aitoff projection, to generate a map having the CPC coordinate system presented on a flat ellipse. The applicant names the map a BNU map (Beijing Normal University Map) (referring to FIG. 3(d)), which is actually a two-dimensional projection image of a standard CPC coordinate system. On the basis of the BNU map, any brain function data related to the scalp surface can be presented in the map, thereby implementing an efficient comparison between different projects, populations, laboratories and even different imaging modalities.

(2) A transcranial brain mapping (TBM for short) model used to connect a cranial location and a brain location is established.

Once the CPC space is established on the individual-level scalp surface, by using a mature balloon inflation model (Okamoto & Dan, 2005), an underlying cortical location c corresponding to the given any point p on the scalp surface may be determined in an individual space (for example, individual 3D MRI image). After all cortical locations are spatially normalized into a standard brain space (that is, MNI space), all (p, c) pairs are aggregated, and a deterministic individual transcranial brain mapping model may be generated. Then, a group-level probabilistic transcranial brain mapping model is generated by integrating all individual transcranial brain mapping models:

$$P(c|p) \quad (3)$$

$p(p_e, p_l) \in$ CPC, $c(x, y, z) \in C$, and C is a subset of the standard brain space and contains all cortical locations related to the transcranial brain mapping technology. The probabilistic transcranial brain mapping model gives the probability of each targeted cortical location c(x y, z) when stimulation or recording starts from any point $p(p_e, p_l)$ having given coordinates on the scalp surface.

Figure 4:
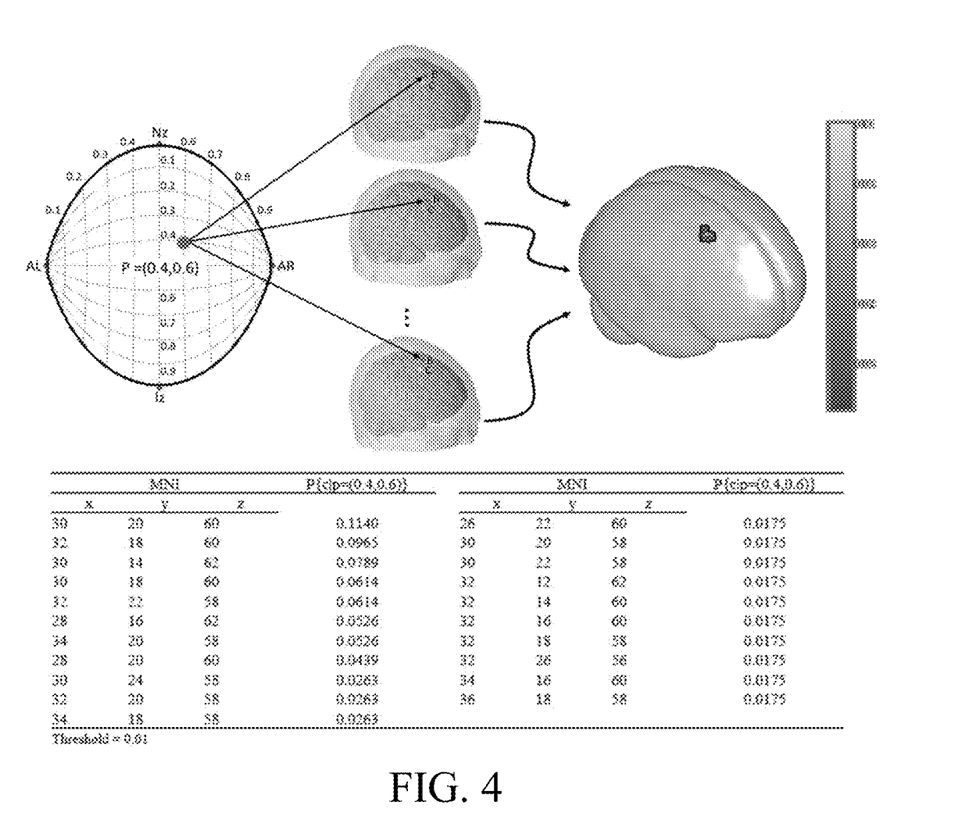
FIG. 4 is a schematic diagram of probabilistic transcranial brain mapping of a single CPC coordinate point.

FIG. 4 shows a probabilistic transcranial brain mapping model corresponding to a single CPC coordinate. When a pair of CPC coordinates is given, for example, P (0.4, 0.6), a corresponding point B may be determined on each individual-level scalp surface, and a location of a cortical projection point C corresponding to the point B is identified in an individual-level magnetic resonance image space by using the mature balloon inflation model. In FIG. 4, a table on the lower half shows corresponding probabilities that any point P (0.4, 0.6) corresponds to different locations in a probabilistic transcranial mapping model.

Mapping from a point in a cranial space to a label in a label space may be considered as two-step mapping. First, mapping is made from the cranial space S to a brain space B. and then mapping is made from the brain space B to the label space L. Because both steps of the mapping are probability mapping, this process may also be considered as a two-step stochastic process. A correspondence between the brain space and a brain region label depends on the structural law of a human brain, and it is assumed that a probability that any point in the brain coordinate space corresponds to each brain region label is deterministic and is unrelated to a corresponding path from the cranial coordinate space to the brain coordinate space. Therefore, this two-step stochastic process has a Markov property.

(3) A transcranial brain atlas is constructed by using a two-step stochastic process in a Markov chain.

A person skilled in the art knows that, the brain atlas is constructed in a in probability framework. For example, a fundamental relationship described by a conventional brain atlas (for example, MNI atlas) is a conditional probability:

$$P(l/b) \quad (4)$$

where b(x, y, z)∈B, and B is the subset of the standard brain space and contains all possible brain tissue points in a brain template of the atlas; and L contains all possible atlas labels, and each atlas label indicates a particular brain region in the brain atlas. For a given pair of and b, P(l|b) indicates a possibility that an atlas label l occurs at a location b in the human brain.

Correspondingly, a fundamental relationship describe by a transcranial brain atlas is also a conditional probability:

$$P(l|p) \quad (5)$$

where $p(p_e, p_l) \in CPC$, and l∈L.

In this embodiment of the present invention, a transcranial brain atlas may be constructed by using a two-step stochastic process in a Markov chain. Specifically, first step: a given point $p(p_e, p_l)$ as input is mapped to a cortical location c(x, y, z) in the standard brain space through probabilistic transcranial mapping P(c|p). Second step: the particular c(x, y, z) is mapped to a label l in a label space L. A researcher or a doctor may independently predict the atlas label l by using the cortical location c(x, y, z) without considering the location $p(p_e, p_l)$ on the scalp surface, and a formula (6) is provided herein:

$$P(l|c,p) = (l|c) \quad (6)$$

Therefore, the Markov chain frequently used by a person skilled in the art is used in the two-step stochastic process. It is assumed that points on a cortex (domain are a subset of points in a brain (domain b), and P(l|p) may be calculated by using P(c|p) in the formula (3) and P(l|b) in the formula (4). Specifically, if p and c are discretized, the Chapman-Kolmogorov equation is indicated as follows:

$$P(l_k \mid p_i) = \sum_{j=1}^{N_c} P(l_k \mid c_j) \times P(c_j \mid p_i) \quad (7)$$

where $p_i$ is a discretized location (that is, any point, similarly below) in a CPC space, where i=1, 2, . . . , $N_p$; $c_j$ is a discretized location of C in the standard brain space, where j=1, 2, . . . , Nc; and $l_k$ is an atlas label of a particular brain atlas, where k=1, 2, . . . , $N_l$.

It should be noted that, the transcranial brain atlas constructed in the foregoing steps is a probability atlas, That is, when a probe performs stimulation or recording at any location p having given coordinates on a scalp surface, a probability that each targeted brain region labeled by l is probed may be given by using the transcranial brain atlas. According to the transcranial brain atlas, invisible intracerebral atlas label information is projected onto a visible scalp, so that a researcher or a doctor may directly use these pieces of brain structure information and function atlas information, thereby greatly improving the function of the brain atlas in the transcranial brain mapping technology.

To sum up, in the present invention, a probabilistic framework based on the two-step Markov chain model is first provided as theoretical foundation of the transcranial brain atlas. The first step is the cranio-cortical mapping from the scalp locations in the CPC space to the underlying cortical locations in the MNI space. The second step is to construct the transcranial brain atlas by using the conventional brain atlas, which is actually mapping from the cortical location in the MNI space to the label space of the atlas. It should be noted that, in the present invention, an extensible transcranial brain atlas model is provided by using the probability framework, and the brain atlas used in the foregoing second step may be replaced with any other brain atlas. In the present invention, only three brain atlases (the BA atlas, the AAL atlas, and the LPBA atlas) based on the macroscopic anatomy are provided to construct the transcranial brain atlas, but similar functional atlases, connection atlases, and other atlases may be used to provide a functional transcranial brain atlas for a particular application.

In the prior art, a primary problem with which the transcranial brain imaging technology is confronted is how to position function information measured on a cranium into a brain atlas, that is, a transcranial positioning problem. Additionally, different from the conventional brain imaging technology, in this technology, in an actual operation, a placement location of a transcranial device (which includes a transcranial brain imaging apparatus or a transcranial brain treatment apparatus) on a cranium further needs to be pre-planned, Therefore, another aspect of the positioning problem of the transcranial brain imaging technology is how to guide individual placement of a transcranial device by using anatomical information in a brain atlas, that is, a transcranial navigation problem.

For the foregoing two problems, an entire solving idea of the present invention is as follows: First, a normalized coordinate system is constructed in a cranial space visible to a transcranial device, and is used to quantitatively depict an entire cranium space that can be covered by an entire transcranial technology. Then, based on large-sample structure image data, a population-level correspondence between the cranium space and the standard brain space and a population-level correspondence between the cranium space and the brain atlas label space are solved. Problems in two aspects of transcranial positioning and transcranial navigation are resolved in this manner. This is specifically described in detail below.

Under the framework of the transcranial brain atlas, positioning for transcranial data in the brain space may be converted into positioning for the transcranial device in the cranial space, so that real-time positioning of the transcranial brain mapping technology becomes possible. Moreover, label information of the transcranial brain atlas is displayed in the cranial space, and this characteristic greatly helps the transcranial brain atlas be superposed onto a scalp surface of an individual to perform display, thereby guiding placement of the transcranial device on a scalp surface of a subject in a visual manner.

To apply the transcranial brain atlas to resolution of the actual positioning and navigation problems of the transcranial brain imaging technology, the present invention provides a surface reconstruction technology based on sparse sampling points, and on the basis of the surface reconstruction technology, an automatic positioning algorithm oriented to a cranial coordinate system is implemented. The automatic positioning algorithm can reconstruct an approximate curved surface of a scalp surface of a subject through only sparse uniform sampling of dozens of points on the scalp surface of the subject, and reconstruct an individual CPC coordinate system of the subject on this curved surface. On the basis of the foregoing automatic positioning algorithm, the present invention proposes an individual-level transcranial brain atlas navigation system based on a cranial coordinate system and a transcranial brain atlas. With the help of a real-time positioning function of a three-dimensional magnetic-field locator, the system may convert, in real time, a location of a stylus moving on a scalp surface of a subject into a CPC coordinate system in which a transcranial brain atlas is located, so as to fuse the transcranial brain atlas in a calculation space and the scalp surface of the subject in a physical space, thereby guiding placement of a transcranial device on the scalp surface by using information about the transcranial brain atlas.

Figure 5:
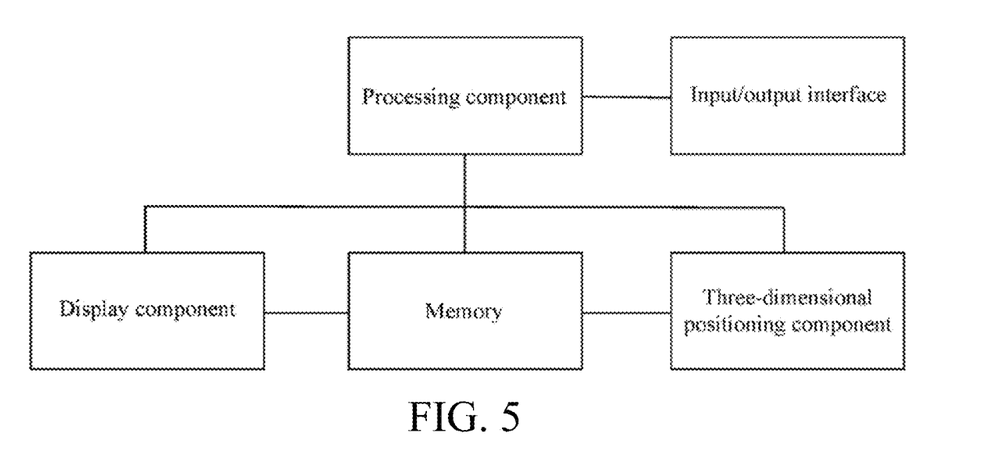
FIG. 5 is a diagram of a structural example of an individual-level transcranial brain atlas navigation system according to the present invention.

As shown in FIG. 5, an individual-level transcranial brain atlas navigation system provided in the present invention includes at least a processing component, a display component, a memory, a three-dimensional positioning component, and an input/output interface. The processing component is connected to the three-dimensional positioning component, the display component, the memory, and the input/output interface, and is configured to control an entire operation of the entire individual-level transcranial brain atlas navigation system and perform all or some steps in the transcranial brain atlas navigation method provided in the present invention. In an exemplary embodiment, the processing component may be implemented by one or more application-specific integrating circuit (ASIC), a digital signal processor (DSP), a digital signal processing device (DSPD), a programmable logic device (VIM), a field programmable gate array (FPGA), a controller, a micro-controller, a microprocessor, or another electronic element, and is configured to perform the foregoing transcranial brain atlas navigation method. The display component is connected to the three-dimensional positioning component, and is configured to display a current physical status of the three-dimensional positioning component on a scalp surface of a subject and a status of the three-dimensional positioning component in a transcranial brain atlas in real time, so as to guide a transcranial device to adjust a placement location on the scalp surface of the subject. The memory is configured to store various types of data to support an operation on the individual-level transcranial brain atlas navigation system. An example of these types of data includes an instruction of any application program or method used for an operation on the individual-level transcranial brain atlas navigation system, or the like. The memory may be implemented by any type of volatile or non-volatile storage device or a combination thereof, for example, a static random access memory (SRAM), an electrically-erasable programmable read-only memory (EEPROM), an erasable programmable read-only memory (EPROM), a programmable read-only memory (PROM), a read-only memory (ROM), a magnetic memory, or a flash memory. The three-dimensional positioning component is configured to reconstruct a geometrical shape of the scalp surface of the subject by using a plurality of discrete points collected from the scalp surface of the subject, and position any point on the scalp surface of the subject in a cranial proportional coordinate system at millimeter-level accuracy. The input/output interface is configured to connect the individual-level transcranial brain atlas navigation system to an external transcranial device, for example, connect the individual-level transcranial brain atlas navigation system to a transcranial brain treatment device or a transcranial brain imaging device. In addition to the foregoing function module, the individual-level transcranial brain atlas navigation system may further include a regular power module and a man-machine interface module (for example, a keyboard or a mouse) that are not specifically described herein.

In an embodiment of the present invention, to obtain space positioning in a physical space, the three-dimensional positioning component uses a Fastrak three-dimensional magnetic-field locator produced by Polhemus Corporation. This three-dimensional magnetic-field locator includes one magnetic-field transmitter and two magnetic-field sensors. One magnetic-field sensor is manufactured into a stylus shape, and the other magnetic-field sensor is of a cube shape. For convenience of description, the magnetic-field sensors are respectively referred to as a stylus and a sensor. When the three-dimensional magnetic-field locator operates, the magnetic-field transmitter generates a local magnetic field, and this magnetic field defines a hemisphere space whose radius is 305 cm. In this hemisphere space, a reference system in which the magnetic-field transmitter is used as an origin can be generated. In this reference system, a spatial location and an attitude of either of the stylus and the sensor may be quantitatively indicated. When the foregoing three-dimensional magnetic-field locator is used, the magnetic-field transmitter is fixed on a bracket behind the subject, the sensor is fixed at a zygomatic location of the subject by using an elastic string, and the stylus is held by an experimenter to calibrate a location on the scalp surface of the subject.

Figure 6:
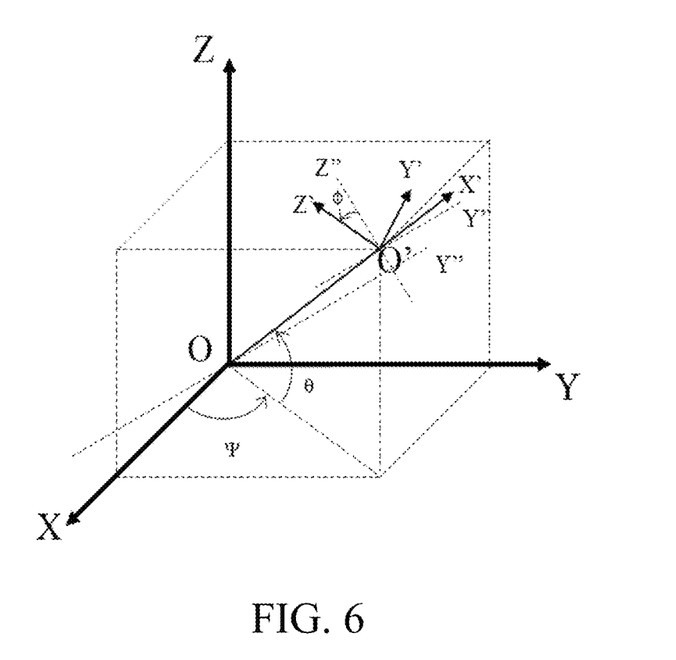
FIG. 6 is a schematic diagram of representation of a spatial location and an attitude of a magnetic-field sensor in a reference system of a magnetic-field transmitter.

For a magnetic-field sensor in the foregoing reference system, a spatial location of the magnetic-field sensor may be first given by O—XYZ coordinates in the reference system. Then, an attitude of the magnetic-field sensor is represented by using an Euler angle. Additionally, the three-dimensional magnetic-field locator also designates one origin and three positive directions, that is, defines a sensor-specific reference system O'—X'Y'Z'. It is assumed that the sensor is initially located on a positive send-axis X of the reference system of the transmitter, and directions of axes X', Y', and Z' are the same as those of axes X, Y, and Z. The sensor may reach a current attitude through three times of rotation. First, on an O—XY plane, the sensor is clockwise rotated by an azimuth $\Psi$ along the axis Z, so that X' is in a same direction as that of a current projection of X' on the O—XY plane. Second, on the O—X' Z plane, the sensor is rotated by an elevation $\theta$ toward a positive direction of the axis Z, so that a direction of X' coincides with a current direction of X', In this case, the axis Z' and the axis Y' are located at Z" and Y" in FIG. 6. Finally, on the O'—Y"Z" plane, the sensor is rotated by a roll $\varphi$ along the axis X', so that Z" and Y" coincide with current axes Z' and Y'. Therefore, in the physical space, the spatial location and the attitude of the magnetic-field sensor may be uniquely described by six dimensions: X, Z, $\Psi$, $\theta$, and $\varphi$.

The three-dimensional magnetic-field locator can position information about a location in the physical space. However, in an actual operation, the head of a subject cannot keep motionless, and therefore collected information about a location on the scalp surface is affected by movement of the head of the subject. Ideally, description of the location on the scalp surface is intended to be established in a reference system that is motionless relative to the head of the subject, To resolve this problem, the sensor in the cube shape is fixed to the scalp surface of the subject, to form a reference system that is motionless relative to the scalp surface, and location information and attitude information of the stylus and the sensor are fused.

Figure 7:
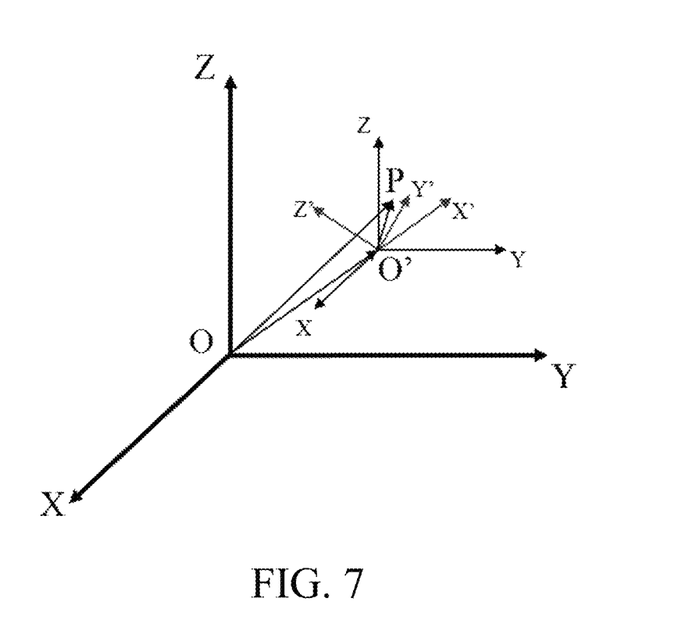
FIG. 7 is a schematic diagram of spatial transformation from a physical coordinate system to a head coordinate system.

As shown in FIG. 7, it is assumed that a coordinate system determined by a magnetic-field transmitter is O—XYZ, a reference system of a sensor is O'—X'Y'Z', and a tip location of a stylus is P; and a reference system O'—XYZ is additionally defined, an origin of the coordinate system is located at O', but directions of axes X. Y, and Z are the same as those of the coordinate system of the magnetic-field transmitter. Coordinates $(x_1, y_1, z_1)$ of a point P in the O—XYZ coordinate system are known, coordinates of a point O' in the O—XYZ coordinate system are $(x_2,y_2,z_2)$, attitude parameters are $(\psi,\theta,\phi)$, and coordinates $(x_3,y_3,z_3)$ of the point P in O'—X'Y'Z' need to be solved.

First, according to a vector relationship between OP, OO', and O'P, the following may be obtained $$(x_1, y_1, z_1)\begin{pmatrix}\overline{OX}\\\overline{OY}\\\overline{OZ}\end{pmatrix} = (x_2, y_2, z_2)\begin{pmatrix}\overline{OX}\\\overline{OY}\\\overline{OZ}\end{pmatrix} + (x_3, y_3, z_3)\begin{pmatrix}\overline{O'X'}\\\overline{O'Y'}\\\overline{O'Z'}\end{pmatrix} \quad (8)$$

that is, $$(x_1 - x_2, y_1 - y_2, z_1 - z_2)\begin{pmatrix}\overline{OX}\\\overline{OY}\\\overline{OZ}\end{pmatrix} = (x_3, y_3, z_3)\begin{pmatrix}\overline{O'X'}\\\overline{O'Y'}\\\overline{O'Z'}\end{pmatrix} \quad (9)$$

$\overline{O'X'}$, $\overline{O'Y'}$, and $\overline{O'Z'}$ are obtained through three times of rotation transformation of $\overline{O'X'}$, $\overline{O'Y'}$, and $\overline{O'Z'}$, and the following transformation relationship exists:

$$A = \begin{pmatrix}1 & 0 & 0\\0 & \cos\phi & \sin\phi\\0 & -\sin\phi & \cos\phi\end{pmatrix} \cdot \begin{pmatrix}\cos\theta & 0 & \sin\theta\\0 & 1 & 0\\-\sin\theta & 0 & \cos\theta\end{pmatrix} \cdot \begin{pmatrix}\cos\psi & \sin\psi & 0\\-\sin\psi & \cos\psi & 0\\0 & 0 & 1\end{pmatrix} \quad (10)$$

Therefore, $$\begin{pmatrix}\overline{O'X'}\\\overline{O'Y'}\\\overline{O'Z'}\end{pmatrix} = A \cdot \begin{pmatrix}\overline{O'X}\\\overline{O'Y}\\\overline{O'Z}\end{pmatrix} \quad (11)$$

that is, $$\begin{pmatrix}\overline{O'X'}\\\overline{O'Y'}\\\overline{O'Z'}\end{pmatrix} = A \cdot \begin{pmatrix}\overline{OX}\\\overline{OY}\\\overline{OZ}\end{pmatrix} \quad (12)$$

The foregoing formula is substituted into the formula (9), to obtain $$(x_1 - x_2, y_1 - y_2, z_1 - z_2)\begin{pmatrix}\overline{OX}\\\overline{OY}\\\overline{OZ}\end{pmatrix} = (x_3, y_3, z_3) \cdot A\begin{pmatrix}\overline{OX}\\\overline{OY}\\\overline{OZ}\end{pmatrix} \quad (13)$$

Therefore, $$(x_3,y_3,z_3)=(x_1-x_2,y_1-y_2,z_1-z_2) \quad (14)$$

The formula (14) gives a transformation relationship of converting a point in the reference system of the transmitter into a head reference system with the help of coordinates and attitude angles of the sensor. With the help of this transformation relationship, any location positioned by the tip of the stylus may be converted into the head reference system moving along with the head of the subject.

Figure 8:
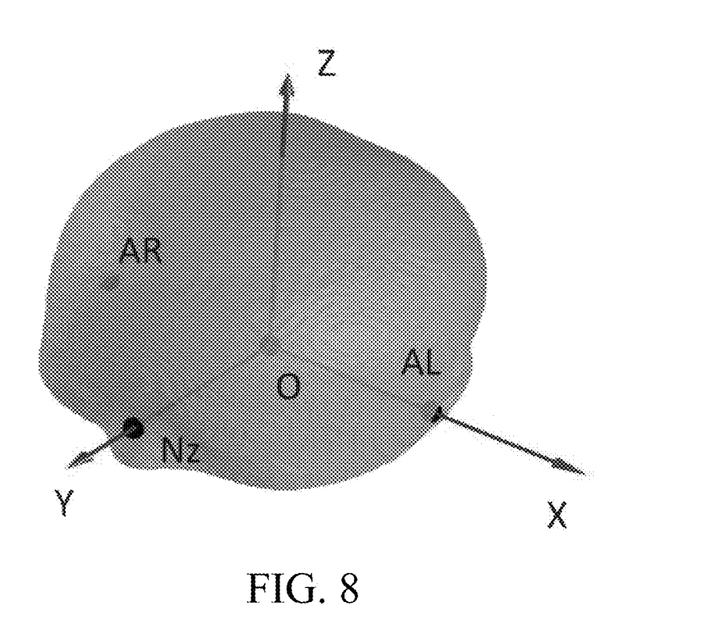
FIG. 8 is a schematic diagram of a nasal-fossa-preauricular coordinate system.

The foregoing point on the scalp surface positioned through the three-dimensional magnetic-field locator is still indicated in a three-dimensional coordinate system. However, a fundamental requirement of the individual-level transcranial brain, atlas navigation system is to position, in an individual CPC coordinate system of the subject, the point indicated in the three-dimensional space. For this purpose, in the present invention, a surface reconstruction algorithm based on sparse sampling is used, and geometrical information of an entire cranium is reconstructed by using sporadic scattering points collected from the cranium. Then, through proportional measurement based on the reconstructed scalp surface, the cranial point indicated in the head reference system is positioned into the individual CPC coordinate system of the subject. Specific description is as follows:

First, sampling is performed on a cranial surface. Sampling points include two parts. The first part is 4 cranial landmark points, that is, Nz, Iz, AL, and AR. The second part is referred to as reconstruction points that are collected by an operator manually on the scalp surface of the subject. Herein, on one hand, the 4 cranial landmark points and the reconstruction points are used together to reconstruct a cranium, and define boundaries of the reconstructed cranium; and on the other hand, during CPC measurement, the 4 cranial landmark points used as 4 measurement benchmark points for CPC system construction are used to position CPC coordinates of a cranial point. After sampling on the cranial surface, a discretized point cloud $P\{x_i,y_i,z_i,i=1, 2, \ldots ,N\}$ of N points is obtained, where the N points are all cranial sampling points including the 4 cranial landmark points. For convenience of implementing the surface reconstruction algorithm, the discretized point cloud is pre-processed, and the pre-processed discretized point cloud is indicated in a nasal-fossa-preauricular coordinate system. As shown in FIG. 8, an origin O of the nasal-fossa-preauricular coordinate system is defined as a midpoint of an AL-AR connection line, and a direction from the point O to Nz is a positive direction of an axis X, a direction from the point O to AL is a positive direction of an axis Y, and a positive direction of an axis Z is defined as a direction of a cross product of the axis X and the axis Y.

Figure 9:
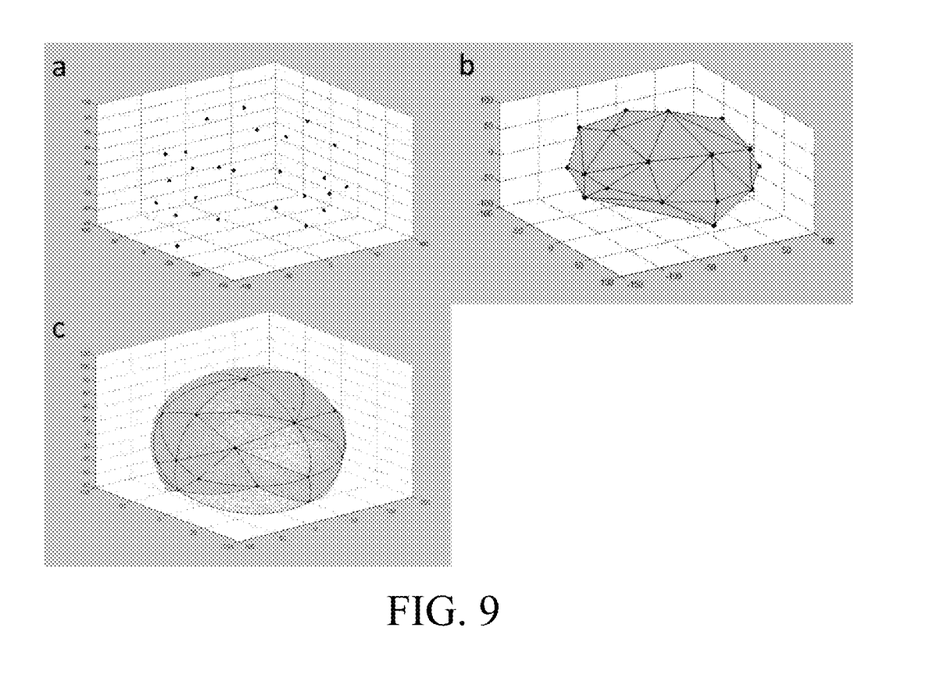
FIG. 9 is a schematic diagram of a scalp surface reconstruction process, where a indicates 21 structureless scattering points collected on a scalp surface, b indicates a topological relationship between sampling points calculated by using, a CRUST algorithm, and c indicates a reconstructed point cloud obtained through spherization processing.

A result obtained through sparse point sampling is a structureless point cloud (a in FIG. 9). By introducing a CRUST algorithm (with reference to Amenta, N., M. Bern, and M. Kamvysselis, A new Voronoi-based surface reconstruction algorithm, in Proceedings of the 25th annual conference on Computer graphics and interactive techniques. 1998, ACM. p. 415-421.), a topological connection between these structureless point clouds is reconstructed, A result obtained through the CRUST algorithm is a triangle patch set, $TP\{(i,j,k)|i,j,k=1, 2, \ldots M\}$ (b in FIG. 9), where i, j, and k are sequence numbers of the midpoint P respectively, and each triplet (i, j, indicates three points topologically neighboring. All triangle patches in TP form a crust of a point cloud P. and the CRUST algorithm may ensure that this crust and an actual cranial surface have a consistent topological structure.

Under sparse sampling, the shape of the crust reconstructed by the point set P is excessively "wizened" relative to the shape of the scalp surface. The shape of a human scalp surface should be a smooth curved surface approximate to an ellipsoid. Therefore, the reconstructed crust is further perfected by introducing a spherization process. In the spherization process, a plurality of times of iterative nonlinear interpolation is performed on each triangle patch. After nonlinear interpolation is performed on all triangle patches in the set TP, a subdivided triangle mesh may be obtained. Vertexes on the triangle mesh are reserved and are recorded as a dense point cloud DP={$x_i,y_i,z_i$|i=1, 2, 3, . . . ,$N_{DP}$} (c in FIG. 9), where $N_{DP}$ is the number of the points in the dense point cloud. For sampling of the recommended order of magnitude being ~10, the order of magnitude of $N_{DP}$ is approximately ~10K.

The dense point cloud DP obtained through reconstruction of the cranial surface is well approximate to the shape of the actual physical scalp surface of the subject. Moreover, in this case, both the dense point cloud DP and 4 cranial benchmark points recorded by the three-dimensional magnetic-field locator are located in a virtual coordinate space, Therefore, a CPC coordinate system may be constructed on this DP, and this CPC coordinate system is considered to be approximate to the CPC system directly obtained on the physical scalp surface of the subject. In this way, if the stylus of the three-dimensional magnetic-field locator newly records any point P on the physical scalp surface of the subject, through, the foregoing coordinate transformation operation, this virtual coordinate space can be entered in real time, and according to the foregoing CPC positioning algorithm, CPC coordinates of the point P may be calculated in real time.

When a navigation operation begins, an operator uses the three-dimensional magnetic-field locator to calibrate 4 cranial benchmark points Nz, Iz AL, and AR on the head of the subject and collect a plurality of sparse points on the scalp of the subject in an even manner. Then, according to the plurality of sampled sparse points, the scalp surface of the subject is reconstructed and CPC coordinates are constructed on the reconstructed scalp surface. Then, the location of the stylus on the scalp surface of the subject is positioned in real time in the CPC coordinates of the subject.

Figure 10:
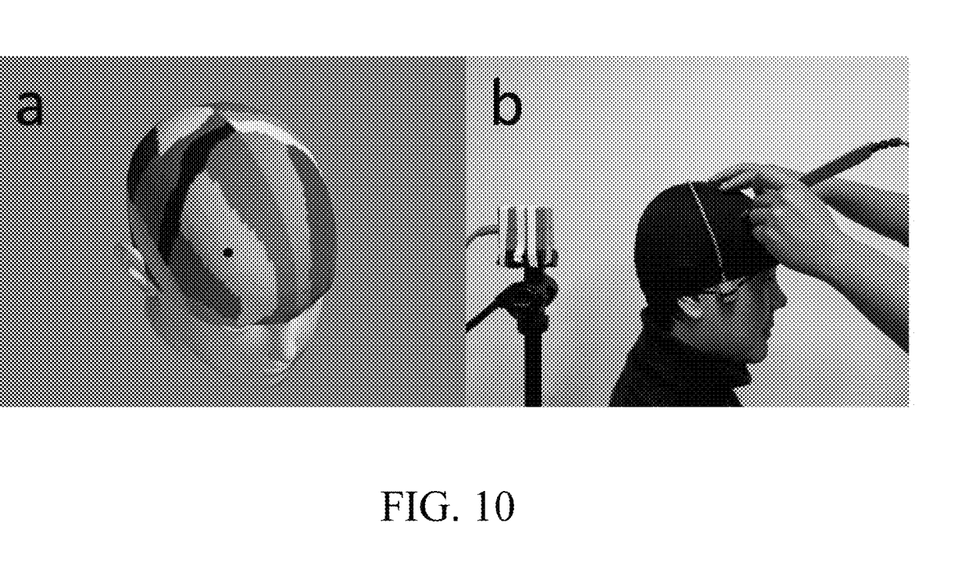
FIG. 10 is a schematic diagram of a use status of an individual-level transcranial brain atlas navigation system according to the present invention, where a is a screenshot displayed on a display component, and b is a schematic diagram of performing an actual operation by an experimenter.

The CPC coordinates on the scalp surface of the subject and CPC coordinates on a 3D head model preset in the individual-level transcranial brain atlas navigation system are in a one-to-one correspondence. Therefore, the location of the stylus on the scalp surface of the subject is displayed in real time on a scalp surface of the 3D head model displayed in the individual-level transcranial brain atlas navigation system. In this way, as the stylus of the three-dimensional magnetic-field locator moves on the scalp surface of the subject, a landmark point on the 3D head model also correspondingly moves. The experimenter navigates, according to a visual feedback given by the individual-level transcranial brain atlas navigation system, the landmark point on the 3D head model to an experimental region of interest by moving the stylus. In this case, the physical location of the stylus on the scalp surface of the subject is a placement location of a transcranial device based on a transcranial brain atlas, as shown in FIG. 10b.

To sum up, for the problem of applying a transcranial brain atlas to guidance of individual placement of a transcranial device, the present invention further provides an individual level transcranial brain atlas navigation system. In an experiment of calibrating 10-20 landmark points, it is verified that in a true experiment guided by the individual-level transcranial brain atlas navigation system, an operator may navigate a cranial target point at millimeter-level accuracy. Finally, feasibility of the individual-level transcranial brain atlas navigation system based on a transcranial brain atlas in a true transcranial brain imaging experiment is verified. An experimental result indicates that, the navigation method and the navigation system based on a transcranial brain atlas can effectively improve coverage accuracy of a near-infrared measurement optrode in a brain region of interest, and consistency between measurement locations on upper cortexes of different persons, thereby improving sensibility of detecting a task-induced brain activity by using a near-infrared technology.

On the other hand, a multi-channel measurement manner is used in a current mainstream functional near-infrared spectroscopy (fNIRS) device, and a brain activity is usually observed by an optrode array having a fixed spacing. This observation is actually a type of discretized "multi-point observation", and different observation points affect each other mainly because of a limitation on the shape of the optrode. The transcranial brain atlas can provide complete cranio-cerebral correspondence information, so as to help the experimenter globally plan the placement location of the optrode. In a true fNIRS experiment, the individual-level transcranial brain atlas navigation system based on a transcranial brain atlas is applied to optrode placement of multi-channel fNIRS. An experimental result indicates that, compared with the conventional 10-20 method, the optrode placement guided by the transcranial brain atlas can effectively improve coverage accuracy of a multi-channel fNIRS measurement channel for a brain region of interest, and consistency between observation location of the measurement channel on different subjects, thereby improving sensibility of detecting a task-induced brain activity through fNIRS. Therefore, the transcranial brain atlas navigation method and navigation system provided in the present invention can also present a distinctive advantage in ensuring coverage accuracy of the optrode at a region level and even in multi-region coverage (a plurality of brain regions is observed by using a same functional near-infrared spectroscopy device).

The individual-characteristic-based transcranial brain atlas generation method, navigation method, and navigation system provided in the present invention are described in detail above. Any obvious change made to the present invention by a person of ordinary skill in the art without departing from the essential spirit of the present invention will constitute a violation of the patent right of the present invention and will bear a corresponding legal liability.

What is claimed is:

1. An individual-characteristic-based cranial surface coordinate system generation method, comprising the following steps:
   (11) identifying five cranial landmarks Nz, Iz, AL, AR, and Cz on an scalp surface;
   (12) defining an intersection curve between the scalp surface and a plane passing through Nz, Cz, and Iz as a cranial equator;
   (13) giving a point p on the scalp surface, wherein a longitude curve can be determined as an intersection curve between the scalp surface and a plane passing through AL, AR, and p, and p' is an intersection point between the cranial equator and the longitude curve; and
   (14) determining the point p on an upper scalp by using a pair of non-negative real numbers (pe, pl):

$p_e = L_{Nz\text{-}p'}/L_e, p_e \in [0,1]$ $p_l = L_{AL\text{-}p}/L_{AL\text{-}p\text{-}AR}, p_l \in [0,1]$ wherein $L_{Nz\text{-}p'}$ is a curve length from Nz to p' along the cranial equator, and $L_e$ is a full length of the cranial equator; and $L_{AL\text{-}p}$ is a curve length from AL to p along the longitude curve whose full length is $L_{AL\text{-}p\text{-}AR}$.

2. The individual-characteristic-based cranial surface coordinate system generation method according to claim 1, further comprising step (15): establishing a CPC space on a standard hemisphere; and planarizing a hemisphere having CPC coordinates by using a Hammer-Aitoff projection, to generate a map having a CPC coordinate system presented on a flat ellipse.

3. An individual-characteristic-based transcranial brain atlas generation method, comprising the following steps:
 (1) creating a cranial surface coordinate system according to the steps in claim 1;
 (2) establishing a transcranial mapping system used to connect a cranial location and a brain location; and
 (3) constructing a transcranial brain atlas by using a two-step stochastic process in a Markov chain.

4. An individual-characteristic-based transcranial brain atlas navigation method, comprising the following steps:
 (1) performing sparse uniform sampling of a plurality of sampling points on a scalp surface of a subject, to reconstruct an approximate curved surface of the scalp surface of the subject;
 (2) establishing a CPC coordinate system on the approximate curved surface; and
 (3) converting, in real time, a location of a stylus moving on the scalp surface of the subject into the CPC coordinate system in which the transcranial brain atlas according to claim 3 is located, and guiding placement of a transcranial device on the scalp surface of the subject by using, information about the transcranial brain atlas.

5. An transcranial brain atlas navigation system, comprising a processing component, a display component, a memory, a three-dimensional positioning component, and an input/output interface, wherein
 the processing component is connected to the three-dimensional positioning component, the display component, the memory, and the input/output interface, and is configured to perform all steps in the individual-characteristic-based transcranial brain atlas navigation method according to claim 4;
 the display component is connected to the three-dimensional position component, and is configured to display a current status of the three-dimensional positioning component on a scalp surface of a subject and a status of the three-dimensional positioning component in a transcranial brain atlas in real time;
 the memory is configured to store various types of data;
 the three-dimensional positioning component is configured to reconstruct an approximate curved surface of the scalp surface of the subject by using a plurality of sampling points collected from the scalp surface of the subject; and
 the input/output interface is configured to connect the transcranial brain atlas navigation system to an external transcranial device.

6. The transcranial brain atlas navigation system according to claim 5, wherein
 the three-dimensional positioning component is a three-dimensional magnetic-field locator, and comprises a magnetic-field transmitter and two magnetic-field sensors, wherein one magnetic-field sensor is of a stylus shape, and the other magnetic-field sensor is of a cube shape.

7. The transcranial brain atlas navigation system according to claim 6, wherein
 when the three-dimensional magnetic-field locator is used, the magnetic-field transmitter is fixed on a bracket behind the subject, the magnetic-field sensor of the cube shape is fixed at a zygomatic location of the subject, and the magnetic-field sensor of the stylus shape is held by an experimenter to calibrate a location on the scalp surface of the subject.

8. The individual-characteristic-based transcranial brain atlas navigation method according to claim 4, wherein
 in step (1), the sampling points comprise two parts, a first part is 4 cranial landmarks Nz, Iz, AL, and AR, and a second part is collected by an operator manually on the scalp surface of the subject.

9. The individual-characteristic-based transcranial brain atlas navigation method according to claim 8, wherein
 discretized point clouds generated based on the sampling points are indicated in a nasal-fossa-preauricular coordinate system, wherein an origin O of the nasal-fossa-preauricular coordinate system is defined as a midpoint of an AL-AR connection line, and a direction from the origin O to Nz is a positive direction of an axis X, a direction from the origin O to AL is a positive direction of an axis Y, and a positive direction of an axis Z is defined as a direction of a cross product of the axis X and the axis Y.

* * * * *